United States Patent [19]

Soula

[11] 4,369,145
[45] Jan. 18, 1983

[54] PREPARATION OF FLUOROBENZENESULFONYL FLUORIDES BY EXCHANGE FLUORINATION

[75] Inventor: Gérard Soula, Meyzieu, France

[73] Assignee: Rhone-Poulenc Industries, Paris, France

[21] Appl. No.: 216,914

[22] Filed: Dec. 16, 1980

[30] Foreign Application Priority Data

Dec. 20, 1979 [FR] France ............................... 79 31220

[51] Int. Cl.³ .......................................... C07C 143/40
[52] U.S. Cl. ............................... 260/543 F; 570/143; 570/147
[58] Field of Search ..................... 260/543 F; 570/143

[56] References Cited

U.S. PATENT DOCUMENTS 3,226,448  12/1965  Gordon et al. .................. 260/543 F

FOREIGN PATENT DOCUMENTS 1004375  9/1965  United Kingdom ................ 570/143
1052462  12/1966  United Kingdom ............ 260/543 F Primary Examiner—Johnnie R. Brown
Assistant Examiner—Frederick W. Pepper
Attorney, Agent, or Firm—Burns, Doane, Swecker and Mathis

[57] ABSTRACT

Fluorobenzenesulfonyl fluorides are prepared by chlorine/fluorine exchange fluorinating a chlorobenzenesulfonyl fluoride with an alkali metal fluoride, in a aprotic polar solvent and at a temperature ranging from about 100° C. to about 240° C.

17 Claims, No Drawings

PREPARATION OF FLUOROBENZENESULFONYL FLUORIDES BY EXCHANGE FLUORINATION

BACKGROUND OF THE INVENTION

1. Field of the Invention:

The present invention relates to the improved preparation of fluorobenzenesulfonyl fluorides and, more especially relates to the preparation of fluorobenzenesulfonyl fluorides by exchange fluorination, i.e., the exchange of a fluorine atom for at least one chlorine atom comprising a chlorobenzenesulfonyl fluoride.

As used herein, by the term "chlorobenzenesulfonyl fluoride" there is intended any compound having the structural formula:

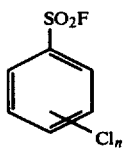
(I)

wherein n ranges from 1 to 5 ($1 \leq n \leq 5$). Those compounds prepared according to the process of the invention have the structural formula:

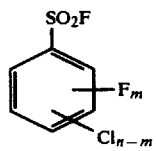
(II)

wherein the fluorine atoms are ortho- and/or para- to the SO$_2$F moiety, m ranges from 1 to 3 ($1 \leq m \leq 3$) and n is as defined above.

The subject process is applicable equally as well to those starting materials (I) wherein the benzene nucleus bears one or more "stable" substituents, in the conditions of the reaction e.g., a hydrocarbon substituent.

2. Description of the Prior Art:

Exchange fluorination reactions are per se well known to this art. Compare G. G. Yakobson et al, *Chemical Abstracts*, Vol. 63, 14740e (1965) and *Chemical Abstracts*, Vol. 66, 94741e (1967) wherein the molten phase reaction of p-chlorobenzenesulfonyl fluoride, 2,4-dichlorobenzenesulfonyl fluoride and 2,4,5-trichlorobenzenesulfonyl fluoride with potassium fluoride is described, same being conducted at temperatures varying between 240° and 290° C. for 25 to 40 hours to respectively obtain p-fluorobenzenesulfonyl fluoride, 2,4-difluorobenzenesulfonyl fluoride and 5-chloro-2,4-difluorobenzenesulfonyl fluoride, in the respective yields of 60%, 55% and 45%.

A process of this type, however, is not entirely satisfactory on an industrial scale, principally because of the elevated temperatures that must necessarily be maintained over very long periods of time.

Cf. French Pat. Nos. 1,360,917 and 1,446,914; Barbour et al, *Industrial and Engineering Chemistry*, Vol. 58, No. 1, 48–55 (1966).

SUMMARY OF THE INVENTION

Accordingly, a major object of the present invention is the provision of an improved exchange fluorination, devoid of the noted disadvantages and drawbacks of the prior art, for the preparation of those substituted and unsubstituted fluorobenzenesulfonyl fluorides having the structural formula:

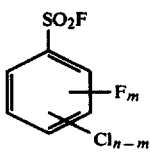
(II)

wherein n ranges from 1 to 5, m ranges from 1 to 3, and the fluorine atoms m are ortho- and/or para- to the —SO$_2$F moiety, by reacting an alkali metal fluoride with chlorobenzenesulfonyl fluoride having the structural formula:

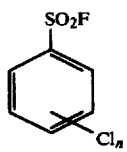
(I)

wherein n is as defined above, the reaction being carried out in an aprotic polar solvent and at a temperature ranging from about 100° C. to about 240° C.

DETAILED DESCRIPTION OF THE INVENTION

More particularly, it has now unexpectedly been found that the subject exchange fluorination can be efficiently carried out in an aprotic polar solvent. Indeed, in the Yakobson references, supra, it is described that the —SO$_2$F group, while electron attracting, is a very weakly activating group (240°-290° C. for 25 to 40 hours). This is due primarily to the fact that during the reaction between a compound of the Formula (I) and an alkali metal fluoride, the F$^-$ ions of KF, for example, are initially exchanged with the fluorine atom comprising the —SO$_2$F group. It is thus necessary to conduct the reaction under such conditions of very high temperatures and for very long reaction times in order to achieve the chlorine/fluorine exchange on the aromatic ring. Hence, it would be apparent to one skilled in this art that, under the aforesaid temperatures and reaction times utilizing the prior art solvents, especially aprotic polar solvents, the introduction of fluorine atoms onto aromatic rings could not be effected by reason of the thermal stability of the solvent.

Accordingly, the unexpected and surprising feature of the invention is that aprotic polar solvents enable the chlorine/fluorine aromatic ring exchange reaction, when utilizing a Formula (I) starting material, to facilely proceed under temperatures and reaction times that are well adapted for conducting the reaction on an industrial scale.

The particular solvent utilized is preferably selected from the group including dimethylformamide, n-methylpyrrolidone, sulfolane, dimethylsulfoxide, hexamethyl phosphorotriamide, acetonitrile, propionitrile and butyronitrile.

Sulfolane is the more preferred solvent.

Advantageously, the reaction is carried out at a temperature ranging from about 130° to about 220° C., with the upper limit on this temperature range being determined vis-a-vis the stability of the solvent. While it is preferred to conduct the reaction at atmospheric pressure, pressures either lower or higher than atmospheric are also within the ambit of the invention.

Preferably, an amount of solvent is used such that the number of moles of starting material, i.e., the chlorobenzenesulfonyl fluoride, per liter of the solvent, ranges from about 0.1 to about 6 moles. Even more preferably, from about 0.2 to about 3 moles are used.

The alkali metal fluoride employed is preferably sodium, potassium, cesium or rubidium fluoride. Potassium fluoride is more preferred because it is the most desirable alkali metal fluoride from an industrial standpoint.

The amount of the alkali metal fluoride used obviously depends on the degree of the chlorine/fluorine exchange that is desired, i.e., on the number of chlorine atoms desired to be replaced.

According to another embodiment of the invention, the subject reaction is carried out in the presence of at least one tertiary amine sequestering agent having the structural formula: ps $$N\text{---}[CHR_1\text{---}CHR_2\text{---}O\text{---}(CHR_3\text{---}CHR_4\text{---}O)_n\text{---}R_5]_3 \quad (III)$$

wherein n is an integer higher than or equal to 0 and less than or equal to approximately 10 ($0 \leq n \leq 10$), $R_1$, $R_2$, $R_3$, $R_4$, which may be the same or different, are each hydrogen or a lower alkyl radical having from 1 to 4 carbon atoms, $R_5$ is alkyl or cycloalkyl radical having 1 to 12 carbon atoms, a phenyl radical or a radical of the formula $-C_mH_{2m}-\phi$, or $C_mH_{2m+1}-\phi-$, with m ranging from about 1 to about 12, and wherein $\phi$ is phenyl.

This particular embodiment of the invention is predicated upon the fact that a sequestering agent having the Formula (III) forms a complex with the alkali metal fluoride that activates the reaction and consequently improves its yield. This improvement in yields is most notable in the case of but slightly active starting materials.

Preferably, in accordance with this particular embodiment of the invention, at least one sequestering agent having the Formula (III) is employed wherein each $R_1$, $R_2$, $R_3$ and $R_4$ is either hydrogen or methyl and $R_5$ and n are as defined above.

Among such preferred sequestering agents, even more preferred are those in which n is higher than or equal to 0 and less than or equal to 3, and wherein $R_5$ is a lower alkyl radical having from 1 to 4 carbon atoms.

Exemplary such compounds are:

(1) Tris(3-oxaheptyl)amine having the formula:

N—(CH₂—CH₂—O—C₄H₉)₃

(2) Tris(3,6-dioxaheptyl)amine having the formula:

N—(CH₂—CH₂—O—CH₂—CH₂—O—CH₃)₃

(3) Tris(3,6,9-trioxadecyl)amine having the formula:

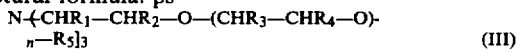

(4) Tris(3,6-dioxaoctyl)amine having the formula:

N—(CH₂—CH₂—O—CH₂—CH₂—O—C₂H₅)₃

(5) Tris(3,6,9-trioxaundecyl)amine having the formula:

N—(CH₂—CH₂—O—CH₂—CH₂—O—CH₂—CH₂—O—C₂H₅)₃

(6) Tris(3,6-dioxanonyl)amine having the formula:

N—(CH₂—CH₂—O—CH₂—CH₂—O—C₃H₇)₃

(7) Tris(3,6,9-trioxadodecyl)amine having the formula:

N—(CH₂—CH₂—O—CH₂—CH₂—O—CH₂—CH₂—O—C₃H₇)₃

(8) Tris(3,6-dioxadecyl)amine having the formula:

N—(CH₂—CH₂—O—CH₂—CH₂—O—C₄H₉)₃

(9) Tris(3,6,9-trioxatridecyl)amine having the formula:

N—(CH₂—CH₂—O—CH₂—CH₂—O—CH₂—CH₂—O—C₄H₉)₃

(10) Tris(3,6-dioxa-4-methylheptyl)amine having the formula:

N—(CH₂—CH₂—O—CHCH₃—CH₂—O—CH₃)₃

(11) Tris(3,6-dioxa-2,4-dimethylheptyl)amine having the formula:

N—(CH₂—CHCH₃—O—CHCH₃—CH₂—O—CH₃)₃.

The amino sequestering agents employed in the process according to the invention are per se known to the prior art. Thus, French Pat. No. 1,302,365 reports the preparation of the tertiary amines N—(CH₂—CH₂—O—CH₃)₃ and N—(CH₂—CH₂—O—CH₂—CH₂—O—CH₃)₃ as by-products of the synthesis of the corresponding primary and secondary amines, such primary and secondary amines being useful intermediates in the preparation of pharmaceuticals, corrosion inhibitors, intermediates in the preparation of agricultural chemicals and emulsifiers. It will be appreciated, though, that whatever the use suggested for any of the amines disclosed in the noted French Pat. No. 1,302,365 patent, including those tertiary amines useful in the present process, such use is completely alien to the field of this invention.

Preferably, the sequestering agent having the Formula (III) is used in an amount such that the molar ratio of sequestering agent to the alkali metal fluoride ranges from about 0.001 to 0.2. This ratio more preferably ranges from about 0.01 to 0.1.

The following compounds are exemplary of the starting materials having the Formula (I): 4-chlorobenzenesulfonyl fluoride, 2-chlorobenzenesulfonyl fluoride, 2,5-dichlorobenzenesulfonyl fluoride, 2,4-dichlorobenzenesulfonyl fluoride, 3,4-dichlorobenzenesulfonyl fluoride, 2,6-dichlorobenzenesulfonyl fluoride, 2,3-dichlorobenzenesulfonyl fluoride, 2,4,5-trichlorobenzenesulfonyl fluoride, 2,3,4-trichlorobenzenesulfonyl fluoride, 2,4,6-trichlorobenzenesulfonyl fluoride, 2,3,4,5-tetrabenzenesulfonyl fluoride, 2,3,5,6-tetrachlorobenzenesulfonyl fluoride, 2,3,4,5-tetrachlorobenzenesulfonyl fluoride and pentachlorobenzenesulfonyl fluoride.

The aforesaid starting materials are used to prepare the following final products having the Formula (II):

4-fluorobenzenesulfonyl fluoride, 2-fluorobenzenesulfonyl fluoride, 2-fluoro-5-chlorobenzenesulfonyl fluoride, 2,4-difluorobenzenesulfonyl fluoride, 4-fluoro-3-chlorobenzenesulfonyl fluoride, 2,6-difluorobenzenesulfonyl fluoride, 2-fluoro-3-chlorobenzenesulfonyl fluoride, 2,4-difluoro-3-benzenesulfonyl fluoride, 2,4-difluoro-3-chlorobenzenesulfonyl fluoride, 2,4,6-trifluorobenzenesulfonyl fluoride, 2,4-difluoro-3,5-dichlorobenzenesulfonyl fluoride, 2,6-difluoro-3,5-dichlorobenzenesulfonyl fluoride, 2,4,6-trifluoro-3-chlorobenzenesulfonyl fluoride, and 2,4,6-trifluoro-3,5-dichlorobenzenesulfonyl fluoride.

It will also be apparent to the skilled artisan that the starting material chlorobenzenesulfonyl fluoride may be replaced by a corresponding chloride which first transforms under the conditions of the reaction into a fluoride having the Formula (I).

The sequestering agents of the Formula (I) used in the process according to the invention are conveniently prepared by condensation of a salt of the formula:

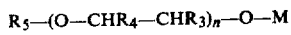

$R_5-(O-CHR_4-CHR_3)_n-O-M$ wherein $R_3$, $R_4$, $R_5$ and n are as defined above and M is an alkali metal selected from the group comprising sodium, potassium and lithium, with an amine having the formula:

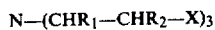

$N-(CHR_1-CHR_2-X)_3$ wherein $R_1$ and $R_2$ are as above defined and X is chlorine or bromine, or with the corresponding hydrochloride or hydrobromide.

The molar ratio of the alkali metal salt to the amine ranges from about 3 to about 5.

The condensation is carried out at a temperature between 100° and 150° C. for 1 to 15 hours in the presence of a solvent which may consist, for example, of chlorobenzene, or preferably an ethylene glycol monoalkylether having the formula:

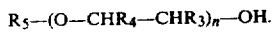

$R_5-(O-CHR_4-CHR_3)_n-OH$.

The process is preferably carried out such that a solution containing 2 to 5 moles of the alkali metal salt is present per liter of solvent.

The mixture upon completion of the reaction principally comprises the tertiary amine of the formula

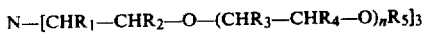

$N-[CHR_1-CHR_2-O-(CHR_3-CHR_4-O)_nR_5]_3$ but also contains a small proportion of the corresponding secondary amine:

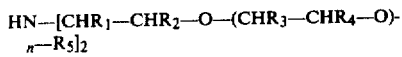

$HN-[CHR_1-CHR_2-O-(CHR_3-CHR_4-O)_n-R_5]_2$ and traces of the primary amine:

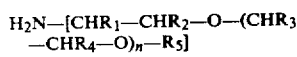

$H_2N-[CHR_1-CHR_2-O-(CHR_3-CHR_4-O)_n-R_5]$

The tertiary, secondary and primary amines are typically present, after distillation, in the ratio of 90:8:2, respectively.

The mixture obtained as described hereinabove may be directly used in the process according to the invention after the first distillation, i.e., while containing the three different types of amines.

Preferably, however, the reaction mix is more rigorously distilled in order to obtain an essentially pure tertiary amine.

The starting materials (I) are prepared utilizing techniques which are conventional to this art, for example, by fluorinating the corresponding chlorobenzenesulfonyl chloride via chlorine/fluorine exchange. It is apparent that the process according to the invention can be applied equally as well to a chlorobenzenesulfonyl chloride which is first converted into a chlorobenzenesulfonyl fluoride under the conditions of reaction, and ultimately into a fluorobenzenesulfonyl fluoride per the invention.

The compounds having the Formula (II) obtained according to the process of the invention are useful intermediates for the preparation of a variety of pharmaceuticals, or for their phytosanitary activity.

In order to further illustrate the present invention and the advantages thereof, the following specific examples are given, it being understood that same are intended only as illustrative and in nowise limitative.

EXAMPLE 1

Preparation of para-fluorobenzenesulfonyl fluoride from para-chlorobenzenesulfonyl fluoride in the presence of a sequestering agent Into a three-necked flask having a capacity of 250 ml, equipped with a mechanical stirrer, a thermometer, a reflux condenser and a calcium chloride trap downstream therefrom, 60 g anhydrous sulfolane, 0.1 mole para-chlorobenzenesulfonyl fluoride (19.5 g), 0.2 mole of anhydrous KF (11.6 g) and 0.01 mole of tris(3,6,9-trioxadecyl) amine (4.5 g), were introduced.

The reaction medium was heated to 200° C. for 5 hours, and then was cooled. The salts were filtered off and the reaction mixture was distilled under reduced pressure.

In this manner, 7 g para-fluorobenzenesulfonyl fluoride and 10.7 g unconverted para-chlorobenzenesulfonyl fluoride were obtained, providing a yield of 88% and a degree of conversion of 45%.

EXAMPLE 2

Preparation of 5-chloro-2,4-difluorobenzenesulfonyl fluoride from 2,4,5-trichlorobenzenesulfonyl chloride in absence of a sequestering agent Into a three-necked, 500 ml flask equipped with a mechanical agitator, a thermometer, a reflux condenser and a calcium chloride trap downstream therefrom, 300 ml anhydrous sulfolane, 0.2 mole of trichlorobenzenesulfonyl chloride (56 g) and 1 mole of anhydrous KF (58 g) were introduced. The reaction mixture was initially heated to 100° C. for 3 hours, during which the 2,4,5-trichlorobenzenesulfonyl fluoride was formed, and then to 160° C. for 11 hours. The reaction medium was cooled and filtered. By distillation, 21 g 5-chloro-2,4-difluorobenzenesulfonyl fluoride were obtained.

EXAMPLE 3

Preparation of 2,4-difluorobenzenesulfonyl fluoride from 2,4-dichlorobenzenesulfonyl chloride (a) Into a three-necked, 500 ml flask, equipped with a mechanical agitator, a thermometer, a reflux condenser and a calcium chloride trap downstream therefrom, 200 g anhydrous sulfolane, 0.1 mole of 2,4-dichlorobenzenesulfonyl chloride (M=245.5) or 24.6 g and 0.5 mole of anhydrous KF or 29 g, were introduced.

The reaction mixture was first heated to 100° C. for 4 hours, and then to 170° C. for 8 hours. The yield of 2,4-difluorobenzenesulfonyl fluoride was 34%.

(b) Under the operating conditions described in the preceding example, 0.01 mole of tris(3,6,9-trioxadecyl-)amine (4.6 g) was added to the reaction medium. After 4 hours at 100° C., and then for 8 hours at 170° C., 2,4-difluorobenzenesulfonyl fluoride was obtained in a yield of 65%.

(c) Into a three-necked, 1 liter flask, equipped with a mechanical agitator, a condenser and a thermometer, 600 g diethylene glycol monomethylether (3,6-dioxa-1-heptanol) or 5 moles, and then 23 g sodium (1 mole) were introduced in small amounts to form sodium 3,6-dioxaheptanolate.

After the sodium had been completely transformed, 51.8 g tris(2-chloroethyl)amine hydrochloride (or 0.215 mole) were added. The reaction mixture was then heated to 130° C. for 8 hours, under agitation, and then cooled and the excess sodium alcoholate neutralized with an aqueous solution of 10% hydrochloric acid. The 3,6-dioxa-1-heptanol was removed by distillation at 130° C., under a pressure 20 mmHg. The reaction mixture was then filtered to remove the sodium chloride and the product was distilled. In this manner, 83 g tris (3,6,9-trioxadecyl)amine were obtained, which compound distilled at 189° C. under 0.1 mmHg.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a fluorobenzenesulfonyl fluoride having the structural formula:

<chemical structure (II): benzene ring with SO$_2$F, F$_m$, Cl$_{n-m}$ substituents> wherein n ranges from 1 to 5, m ranges from 1 to 3 and the fluorine atoms m are ortho- and/or para- to the —SO$_2$F moiety, comprising exchange fluorinating a chlorobenzenesulfonyl fluoride having the structural formula:

<chemical structure (I): benzene ring with SO$_2$F and Cl$_n$ substituents> wherein n is as defined above, with an alkali metal fluoride, in an aprotic polar solvent and at a temperature ranging from about 100° C. to about 240° C., said exchange fluorination being conducted in the presence of at least one tertiary amine sequestering agent having the formula:

$$N\text{-}(CHR_1\text{---}CHR_2\text{---}O\text{-}(CHR_3\text{---}CHR_4\text{---}O)_n\text{-}R_5)_3 \quad (III)$$

where $0 \leq n \leq 10$, $R_1$, $R_2$, $R_3$ and $R_4$, which may be the same or different, are each hydrogen or lower alkyl, $R_5$ is alkyl or cycloalkyl having from 1 to 12 carbon atoms, phenyl, —$C_mH_{2m}$—$\phi$ or $C_mH_{2m+1}$—$\phi$—, with m ranging from about 1 to 12 and $\phi$ being phenyl.

2. The process as defined by claim 1, wherein the aprotic polar solvent is selected from the group consisting of dimethylformamide, n-methylpyrrolidone, sulfolane, dimethylsulfoxide, hexamethyl phosphoramide, acetonitrile, propionitrile and butyronitrile.

3. The process as defined by claim 2, wherein the aprotic polar solvent is sulfolane.

4. The process as defined by claim 1, said exchange fluorination being conducted at a temperature ranging from about 130° C. to about 220° C.

5. The process as defined by claim 1, the chlorobenzenesulfonyl fluoride (I) being present in an amount of from about 0.1 to about 6 moles per liter of the aprotic polar solvent.

6. The process as defined by claim 5, the chlorobenzenesulfonyl fluoride (I) being present in an amount of from about 0.2 to about 3 moles per liter of the aprotic polar solvent.

7. The process as defined by claim 1, wherein the sequestering agent (III), $R_1$, $R_2$, $R_3$ and $R_4$, which may be the same or different, are each hydrogen or methyl.

8. The process as defined by claim 1, wherein the sequestering agent (III), $0 \leq n \leq 5$.

9. The process as defined by claim 1, wherein the sequestering agent (III), $R_5$ is alkyl having from 1 to 4 carbon atoms.

10. The process as defined by claim 1, wherein the sequestering agent (III), $R_1$, $R_2$, $R_3$ and $R_4$, which may be the same or different, are each hydrogen or methyl, $0 \leq n \leq 3$, and $R_5$ is alkyl having from 1 to 4 carbon atoms.

11. The process as defined by claim 10, wherein the sequestering agent (III) is tris(3,6,9-trioxadecyl)amine having the formula:

$$N\text{-}(CH_2\text{---}CH_2\text{---}O\text{---}CH_2\text{---}CH_2\text{---}O\text{---}CH_2\text{---}CH_2\text{---}O\text{---}CH_3)_3.$$

12. The process as defined by claim 1, the sequestering agent (III) being selected from the group consisting of tris(3-oxaheptyl)amine, tris(3,6-dioxaheptyl)amine, tris(3,6,9-trioxadecyl)amine, tris(3,6-dioxaoctyl)amine, tris(3,6,9-trioxaundecyl)amine, tris(3,6-dioxanonyl)amine, tris(3,6,9-trioxadodecyl)amine, tris(3,6-dioxadecyl)amine, tris(3,6,9-trioxatridecyl)amine, tris(3,6-dioxa-4-methylheptyl)amine, and tris(3,6-dioxa-2,4-dimethylheptyl)amine.

13. The process as defined by claim 1, wherein the alkali metal fluoride is selected from the group consisting of sodium fluoride, potassium fluoride, cesium fluoride and rubidium fluoride.

14. The process as defined by claim 13, wherein the alkali metal fluoride is potassium fluoride.

15. The process as defined by claim 1, the sequestering agent (III) being present in a molar ratio to the alkali metal fluoride ranging from about 0.001 to about 0.02.

16. The process as defined by claim 15, the sequestering agent (III) being present in a molar ratio to the alkali metal fluoride ranging from about 0.01 to about 0.1.

17. The process as defined by claim 1, the chlorobenzenesulfonyl fluoride (I) being selected from the group consisting of 4-chlorobenzenesulfonyl fluoride, 2- chlorobenzenesulfonyl fluoride, 2,5-dichlorobenzenesulfonyl fluoride, 2,4-dichlorobenzenesulfonyl fluoride, 3,4-dichlorobenzenesulfonyl fluoride, 2,6-dichlorobenzenesulfonyl fluoride, 2,3-dichlorobenzenesulfonyl fluoride, 2,4,5-trichlorobenzenesulfonyl fluoride, 2,3,4-trichlorobenzenesulfonyl fluoride, 2,4,6-trichlorobenzenesulfonyl fluoride, 2,3,5,6-tetrachlorobenzenesulfonyl fluoride, 2,3,4,5-tetrachlorobenzenesulfonyl fluoride and pentachlorobenzenesulfonyl fluoride.

* * * * *